(12) United States Patent
Farritor et al.

(10) Patent No.: US 10,722,319 B2
(45) Date of Patent: Jul. 28, 2020

(54) RELEASABLE ATTACHMENT DEVICE FOR COUPLING TO MEDICAL DEVICES AND RELATED SYSTEMS AND METHODS

(71) Applicant: Virtual Incision Corporation, Lincoln, NE (US)

(72) Inventors: Shane Farritor, Lincoln, NE (US); Nathan Wood, Lincoln, NE (US); Jeff Shasho, Brooklyn, NY (US)

(73) Assignee: Virtual Incision Corporation, Lincoln, NE (US)

( * ) Notice: Subject to any disclaimer, the term of this patent is extended or adjusted under 35 U.S.C. 154(b) by 170 days.

(21) Appl. No.: 15/842,230

(22) Filed: Dec. 14, 2017

(65) Prior Publication Data

US 2018/0161122 A1      Jun. 14, 2018

Related U.S. Application Data

(60) Provisional application No. 62/433,837, filed on Dec. 14, 2016.

(51) Int. Cl.
| | |
|---|---|
| *A61B 1/32* | (2006.01) |
| *A61B 90/50* | (2016.01) |
| *A61M 39/12* | (2006.01) |
| *A61B 90/57* | (2016.01) |
| *A61M 5/14* | (2006.01) |
| *A61M 39/10* | (2006.01) |
| *A61B 17/00* | (2006.01) |

(52) U.S. Cl.
CPC .............. *A61B 90/50* (2016.02); *A61B 90/57* (2016.02); *A61M 5/1415* (2013.01); *A61M 39/12* (2013.01); *A61B 2017/0046* (2013.01); *A61B 2017/00477* (2013.01); *A61M 39/1011* (2013.01)

(58) Field of Classification Search
USPC ........................ 606/324–328, 147, 151, 157
See application file for complete search history.

(56) References Cited

U.S. PATENT DOCUMENTS

| | | |
|---|---|---|
| 3,870,264 A | 3/1975 | Robinson |
| 3,989,952 A | 11/1976 | Timberlake et al. |
| 4,258,716 A | 3/1981 | Sutherland |
| 4,278,077 A | 7/1981 | Mizumoto |
| 4,538,594 A | 9/1985 | Boebel et al. |

(Continued)

FOREIGN PATENT DOCUMENTS

| | | |
|---|---|---|
| CN | 102821918 | 12/2012 |
| DE | 102010040405 | 3/2012 |

(Continued)

OTHER PUBLICATIONS

Franzino, "The Laprotek Surgical System and the Next Generation of Robotics," Surg Clin North Am, 2003 83(6): 1317-1320.

(Continued)

*Primary Examiner* — Sameh R Boles
(74) *Attorney, Agent, or Firm* — Davis, Brown, Koehn, Shors & Roberts, P.C.; Sean D. Solberg

(57) ABSTRACT

The various embodiments herein relate to releasable attachment devices for use with surgical tools that include a fixed jaw fixedly coupled to a joint housing, a moveable jaw rotationally coupled to the joint housing, and an actuation mechanism operably coupled to the joint housing.

19 Claims, 6 Drawing Sheets

(56) References Cited

U.S. PATENT DOCUMENTS

| | | |
|---|---|---|
| 4,568,311 A | 2/1986 | Miyake |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,922,755 A | 5/1990 | Oshiro et al. |
| 4,922,782 A | 5/1990 | Kawai |
| 4,990,050 A | 2/1991 | Tsuge et al. |
| 5,019,968 A | 5/1991 | Wang et al. |
| 5,172,639 A | 12/1992 | Wiesman et al. |
| 5,195,388 A | 3/1993 | Zona et al. |
| 5,201,325 A | 4/1993 | McEwen et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,388,528 A | 2/1995 | Pelrine et al. |
| 5,436,542 A | 7/1995 | Petelin et al. |
| 5,441,494 A | 8/1995 | Ortiz |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Takayama et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tiemey et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byme et al. |
| 6,692,485 B1 | 2/2004 | Brock et al. |
| 6,699,177 B1 | 3/2004 | Wang et al. |

(56) References Cited

U.S. PATENT DOCUMENTS

| | | |
|---|---|---|
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,588,537 B2 | 9/2009 | Bass |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,021,358 B2 | 9/2011 | Doyle et al. |
| 8,182,469 B2 | 5/2012 | Anderson et al. |
| 8,353,897 B2 | 1/2013 | Doyle et al. |
| 9,089,353 B2 | 7/2015 | Farritor et al. |
| 2001/0018591 A1 | 8/2001 | Brook et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | de la Torre et al. |
| 2002/0065507 A1 | 5/2002 | Zadno-Azizi |
| 2002/0091374 A1 | 6/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |

(56) References Cited

U.S. PATENT DOCUMENTS

| | | |
|---|---|---|
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 6/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth |
| 2004/0138525 A1 | 7/2004 | Saadat et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Julius et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0045803 A1 | 2/2008 | Williams et al. |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1 | 5/2008 | de la Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 6/2008 | Rioux et al. |
| 2008/0164079 A1 | 7/2008 | Ferren et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1 | 8/2010 | Manzo et al. |
| 2010/0245549 A1 | 9/2010 | Allen et al. |
| 2010/0262162 A1 | 10/2010 | Omori |
| 2010/0292691 A1 | 11/2010 | Brogna |
| 2010/0318059 A1 | 12/2010 | Farritor et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0098529 A1 | 4/2011 | Ostrovsky et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0264078 A1 | 10/2011 | Lipow et al. |
| 2011/0270443 A1 | 11/2011 | Kamiya et al. |
| 2012/0035582 A1 | 2/2012 | Nelson et al. |
| 2012/0109150 A1 | 5/2012 | Quaid et al. |
| 2012/0116362 A1 | 5/2012 | Kieturakis |
| 2012/0179168 A1 | 7/2012 | Farritor et al. |
| 2012/0253515 A1 | 10/2012 | Coste-Maniere et al. |

(56) References Cited

U.S. PATENT DOCUMENTS

| | | | |
|---|---|---|---|
| 2013/0131695 | A1 | 5/2013 | Scarfogliero et al. |
| 2013/0345717 | A1 | 12/2013 | Markvicka et al. |
| 2014/0039515 | A1 | 2/2014 | Mondry et al. |
| 2014/0046340 | A1 | 2/2014 | Wilson et al. |
| 2014/0058205 | A1 | 2/2014 | Frederick et al. |
| 2014/0303434 | A1 | 10/2014 | Farritor et al. |
| 2015/0051446 | A1 | 2/2015 | Farritor et al. |
| 2016/0228154 | A1 | 8/2016 | Mickiewicz et al. |
| 2017/0035526 | A1* | 2/2017 | Farritor .................. A61B 34/30 |

FOREIGN PATENT DOCUMENTS

| | | |
|---|---|---|
| EP | 1354670 | 10/2003 |
| EP | 2286756 | 2/2011 |
| EP | 2286756 A1 | 2/2011 |
| EP | 2329787 | 6/2011 |
| EP | 2563261 | 3/2013 |
| JP | 05-115425 | 5/1993 |
| JP | 2006508049 | 9/1994 |
| JP | 07-016235 | 1/1995 |
| JP | 07-136173 | 5/1995 |
| JP | 7306155 | 11/1995 |
| JP | 08-224248 | 9/1996 |
| JP | 2001500510 | 1/2001 |
| JP | 2001505810 | 5/2001 |
| JP | 2003220065 | 8/2003 |
| JP | 2004144533 | 5/2004 |
| JP | 2004-180781 | 7/2004 |
| JP | 2004322310 | 11/2004 |
| JP | 2004329292 | 11/2004 |
| JP | 2006507809 | 3/2006 |
| JP | 2009106606 | 5/2009 |
| JP | 2010533045 | 10/2010 |
| JP | 2010536436 | 12/2010 |
| JP | 2011504794 | 2/2011 |
| JP | 2011045500 | 3/2011 |
| JP | 2011115591 | 6/2011 |
| WO | 199221291 | 5/1991 |
| WO | 2001089405 | 11/2001 |
| WO | 2002082979 | 10/2002 |
| WO | 2002100256 | 12/2002 |
| WO | 2005009211 | 7/2004 |
| WO | 2005044095 | 5/2005 |
| WO | 2006052927 | 8/2005 |
| WO | 2006005075 | 1/2006 |
| WO | 2006079108 | 1/2006 |
| WO | 2006079108 | 7/2006 |
| WO | 2007011654 | 1/2007 |
| WO | 2007111571 | 10/2007 |
| WO | 2007149559 | 12/2007 |
| WO | 2009023851 | 2/2009 |
| WO | 2009144729 | 12/2009 |
| WO | 2010050771 | 5/2010 |
| WO | 2011075693 | 6/2011 |
| WO | 2011118646 | 9/2011 |
| WO | 2011135503 | 11/2011 |
| WO | 2013009887 | 1/2013 |
| WO | 2014011238 | 1/2014 |

OTHER PUBLICATIONS

Franklin et al., "Prospective Comparison of Open vs. Laparoscopic Colon Surgery for Carcinoma: Five-Year Results," Dis Colon Rectum, 1996; 39: S35-S46.
Flynn et al, "Tomorrow's surgery: micromotors and microrobots for minimally invasive procedures," Minimally Invasive Surgery & Allied Technologies, 1998; 7(4): 343-352.
Fireman et al., "Diagnosing small bowel Crohn's desease with wireless capsule endoscopy," Gut 2003; 52: 390-392.
Fearing et al., "Wing Transmission for a Micromechanical Flying Insect," Proceedings of the 2000 IEEE International Conference to Robotics & Automation, Apr. 2000; 1509-1516.
Faraz et al., "Engineering Approaches to Mechanical and Robotic Design for Minimaly Invasive Surgery (MIS)," Kluwer Academic Publishers (Boston), 2000, 13pp.
Falcone et al., "Robotic Surgery," Clin. Obstet. Gynecol. 2003, 46(1): 37-43.
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Dumpert et al., "Improving in Vivo Robot Visioin Quality," from the Proceedings of Medicine Meets Virtual Realtiy, Long Beach, CA, Jan. 26-29, 2005. 1 pg.
Dakin et al., "Comparison of laparoscopic skills performance between standard instruments and two surgical robotic systems," Surg Endosc., 2003; 17: 574-579.
Cuschieri, "Technology for Minimal Access Surgery," BMJ, 1999, 319: 1-6.
Grady, "Doctors Try New Surgery for Gallbladder Removal," The New York Times, Apr. 20, 2007, 3 pp.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Chanthasopeephan et al., (2003), "Measuring Forces in Liver Cutting: New Equipment and Experimenal Results," Annals of Biomedical Engineering 31: 1372-1382.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Guber et al., "Miniaturized Instrument Systems for Minimally Invasive Diagnosis and Therapy," Biomedizinische Technic. 2002, Band 47, Erganmngsband 1: 198-201.
Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Atmel 80C5X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.

(56) References Cited

OTHER PUBLICATIONS

Calafiore et al., Multiple Arterial Conduits Without Cardiopulmonary Bypass: Early Angiographic Results,: Ann Thorac Surg, 1999; 67: 450-456.

Camarillo et al., "Robotic Technology in Surgery: Past, Present and Future," The American Journal of Surgery, 2004; 188: 2S-15.

Cavusoglu et al., "Telesurgery and Surgical Simulation: Haptic Interfaces to Real and Virtual Surgical Environments," In McLaughliin, M.L., Hespamha, J.P., and Sukhatme, G., editors. Touch in virtual environments, IMSC Series in Multimedia 2001, 28pp.

Dumpert et al, "Stereoscopic in Vivo Surgical Robots," IEEE Sensors Special Issue on In Vivo Sensors for Medicine, Jan. 2007, 10 pp.

Green, "Telepresence Surgery", Jan. 1, 1995, Publisher: IEEE Engineering in Medicine and Biology.

Cleary et al., "State of the Art in Surgical Rootics: Clinical Applications and Technology Challenges", "Computer Aided Surgery", Jan. 1, 2002, pp. 312-328, vol. 6.

Stoianovici et al., "Robotic Tools for Minimally Invasive Urologic Surgery", Jan. 1, 2002, pp. 1-17.

\* cited by examiner

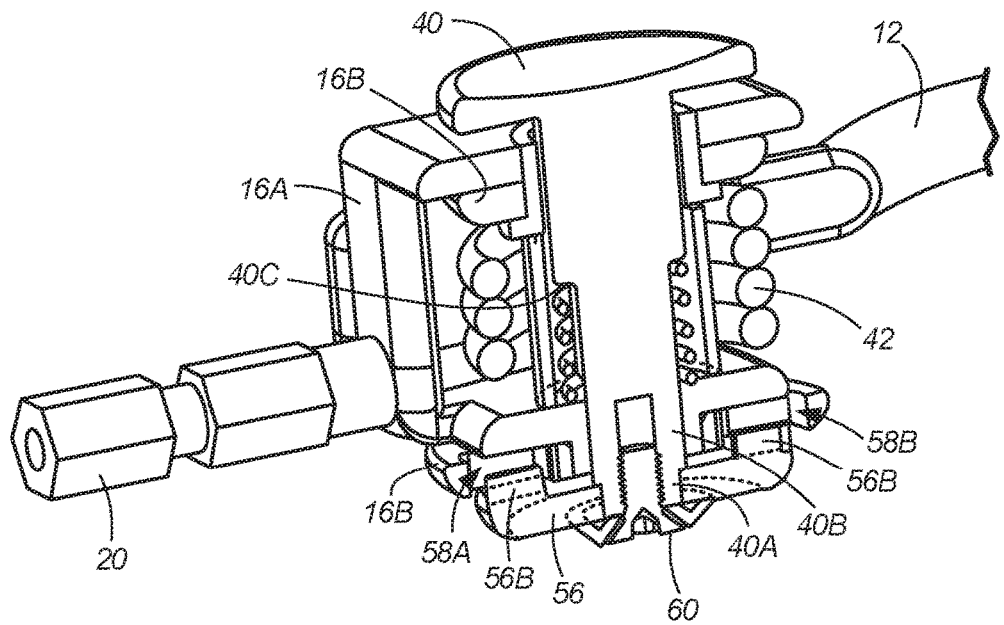
FIG. 3C
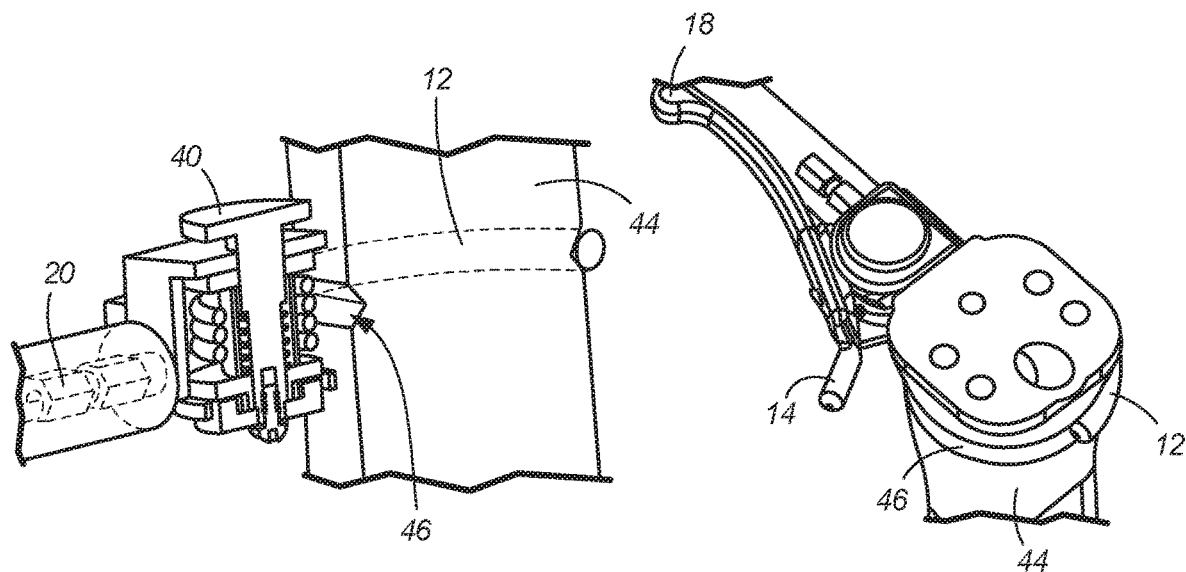
FIG. 4A
FIG. 4B

RELEASABLE ATTACHMENT DEVICE FOR COUPLING TO MEDICAL DEVICES AND RELATED SYSTEMS AND METHODS

CROSS-REFERENCE TO RELATED APPLICATION(S)

This application claims the benefit under 35 U.S.C. § 119(e) to U.S. Provisional Application 62/433,837, filed Dec. 14, 2016 and entitled "Releasable Attachment Device for Coupling to Medical Devices and Related Systems and Methods," which is hereby incorporated herein by reference in its entirety.

FIELD OF THE INVENTION

The various embodiments herein relate to support devices for supporting various types of medical devices and more specifically to releasable attachment devices for use in releasably holding a medical device on a support device.

BACKGROUND OF THE INVENTION

Known support devices firmly retain and maintain the position of a medical device before and during a surgical procedure. However, most such known devices can only fixedly retain the medical device in a position that is not adjustable.

There is a need in the art for an improved releasable attachment device for coupling a medical device to a support device.

BRIEF SUMMARY OF THE INVENTION

Discussed herein are various releasable attachment device that can be used to releasably couple a medical device to a support device.

In Example 1, a releasable attachment device for use with surgical tools comprises a fixed jaw fixedly coupled to a joint housing, a moveable jaw rotationally coupled to the joint housing, the moveable jaw comprising an open position and a closed position, an actuation mechanism operably coupled to the joint housing, wherein the actuation mechanism comprises a locked position and a released position, and an actuation structure operably coupled to the moveable jaw.

Example 2 relates to the releasable attachment device according to Example 1, further comprising a coupling component fixedly coupled to the joint housing, wherein the coupling component comprises a coupling structure constructed and arranged to couple to an external support device.

Example 3 relates to the releasable attachment device according to Example 1, further comprising a tension component operably coupled to the joint housing, wherein the tension component is constructed and arranged to urge the moveable jaw toward the closed position.

Example 4 relates to the releasable attachment device according to Example 1, further comprising a tension component operably coupled to the actuation mechanism, wherein the tension component is constructed and arranged to urge the actuation mechanism toward the locked position.

Example 5 relates to the releasable attachment device according to Example 1, wherein the fixed jaw and moveable jaw are constructed and arranged to couple with a surgical tool in a groove defined around an outer surface of the surgical tool.

Example 6 relates to the releasable attachment device according to Example 1, wherein the joint housing comprises a stationary joint structure comprising a first opening defined therethrough, a pivotable joint structure comprising a second opening defined therethrough and at least one rotational coupling mechanism defined therein, the actuation mechanism disposed through the first and second openings, wherein the actuation mechanism is rotationally coupled to the first joint structure, and a locking structure rotationally coupled to a distal end of the actuation mechanism and detachably coupleable with the at least one rotational coupling mechanism.

Example 7 relates to the releasable attachment device according to Example 6, wherein the released position comprises the actuation mechanism positioned distally in relation to the locked position.

Example 8 relates to the releasable attachment device according to Example 6, wherein the locking structure is coupled to the at least one rotational coupling mechanism when the actuation mechanism is in the locked position and wherein the locking structure is not coupled to the at least one rotational coupling mechanism when the actuation mechanism is in the released position.

Example 9 relates to the releasable attachment device according to Example 6, wherein the pivotable joint structure is rotatable in relation to the stationary joint structure when the actuation mechanism is in the released position.

In Example 10, a releasable attachment device for use with surgical tools comprises a joint housing, a fixed jaw fixedly coupled to the first joint structure, a moveable jaw fixedly coupled to the second joint structure, the moveable jaw comprising an open position and a closed position, and an actuation structure operably coupled to the moveable jaw. The joint housing has a first joint structure comprising a first opening defined therethrough, a second joint structure comprising a second opening defined therethrough and at least one rotational coupling mechanism defined therein, an actuation mechanism disposed through the first and second openings, wherein the actuation mechanism is rotationally coupled to the first joint structure and wherein the actuation mechanism comprises an undepressed axial position and a depressed axial position, and a locking structure rotationally coupled to a distal end of the actuation mechanism and detachably coupleable with the at least one rotational coupling mechanism.

Example 11 relates to the releasable attachment device according to Example 10, further comprising a coupling component fixedly coupled to the joint housing, wherein the coupling component comprises a coupling structure constructed and arranged to couple to an external support device.

Example 12 relates to the releasable attachment device according to Example 10, further comprising a tension component operably coupled to the first joint structure and the second joint structure, wherein the tension component is constructed and arranged to urge the moveable jaw toward the closed position.

Example 13 relates to the releasable attachment device according to Example 10, further comprising a tension component operably coupled to the actuation mechanism, wherein the tension component is constructed and arranged to urge the actuation mechanism toward the undepressed axial position.

Example 14 relates to the releasable attachment device according to Example 10, wherein the fixed jaw and moveable jaw are constructed and arranged to couple with a surgical tool in a groove defined around an outer surface of the surgical tool.

Example 15 relates to the releasable attachment device according to Example 10, wherein the depressed axial position comprises the actuation mechanism positioned distally in relation to the undepressed axial position.

Example 16 relates to the releasable attachment device according to Example 10, wherein the locking structure is coupled to the at least one rotational coupling mechanism when the actuation mechanism is in the undepressed axial position and wherein the locking structure is not coupled to the at least one rotational coupling mechanism when the actuation mechanism is in the depressed axial position.

Example 17 relates to the releasable attachment device according to Example 10, wherein the second joint structure is rotatable in relation to the first joint structure when the actuation mechanism is in the depressed axial position.

In Example 18, a releasable attachment device for use with surgical tools comprises a housing, a fixed jaw fixedly coupled to the first joint structure, a moveable jaw fixedly coupled to the second joint structure, the moveable jaw comprising an open position and a closed position, and an actuation structure operably coupled to the moveable jaw. The housing comprises a first joint structure and a second joint structure. The first joint structure comprises a first strut comprising a first opening, and a second strut comprising a second opening, wherein the second opening comprises a first rotational coupling mechanism. The second joint structure comprises a third strut comprising a third opening, and a fourth strut comprising a fourth opening and a second rotational coupling mechanism. The housing further comprises an actuation mechanism comprising a mechanism body and a button coupled thereto, wherein the mechanism body is disposed through the first, second, third, and fourth openings, wherein the mechanism body is coupled to the rotational coupling mechanism such that the mechanism body is rotationally constrained to the second strut, and wherein the actuation mechanism comprises an undepressed axial position and a depressed axial position. Further, the housing also comprises a locking structure rotationally coupled to a distal end of the mechanism body and detachably coupleable with the second rotational coupling mechanism, wherein the locking structure is coupled to the second rotational coupling mechanism when the actuation mechanism is in the undepressed axial position and wherein the locking structure is not coupled to the second rotational coupling mechanism when the actuation mechanism is in the depressed axial position, wherein the second joint structure is rotatable in relation to the first joint structure when the actuation mechanism is in the depressed axial position.

Example 19 relates to the releasable attachment device according to Example 18, further comprising a coupling component fixedly coupled to the housing, wherein the coupling component comprises a coupling structure constructed and arranged to couple to an external support device.

Example 20 relates to the releasable attachment device according to Example 18, further comprising a tension component operably coupled to the first and second joint structures, wherein the tension component is constructed and arranged to urge the moveable jaw toward the closed position.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 3C is a cross-sectional perspective view of the various components of the releasable attachment device of FIG. 3A, according to one embodiment.

FIG. 4A is a cross-sectional perspective view of the various components of a releasable attachment device coupled to a robotic device, according to one embodiment.

FIG. 4B is a perspective view of the releasable attachment device of FIG. 4A, according to one embodiment.

DETAILED DESCRIPTION

The various embodiments disclosed herein relate to a releasable attachment or retention device for stably and removably coupling to a medical device, including, for example, a robotic surgical device.

Figure 1A:
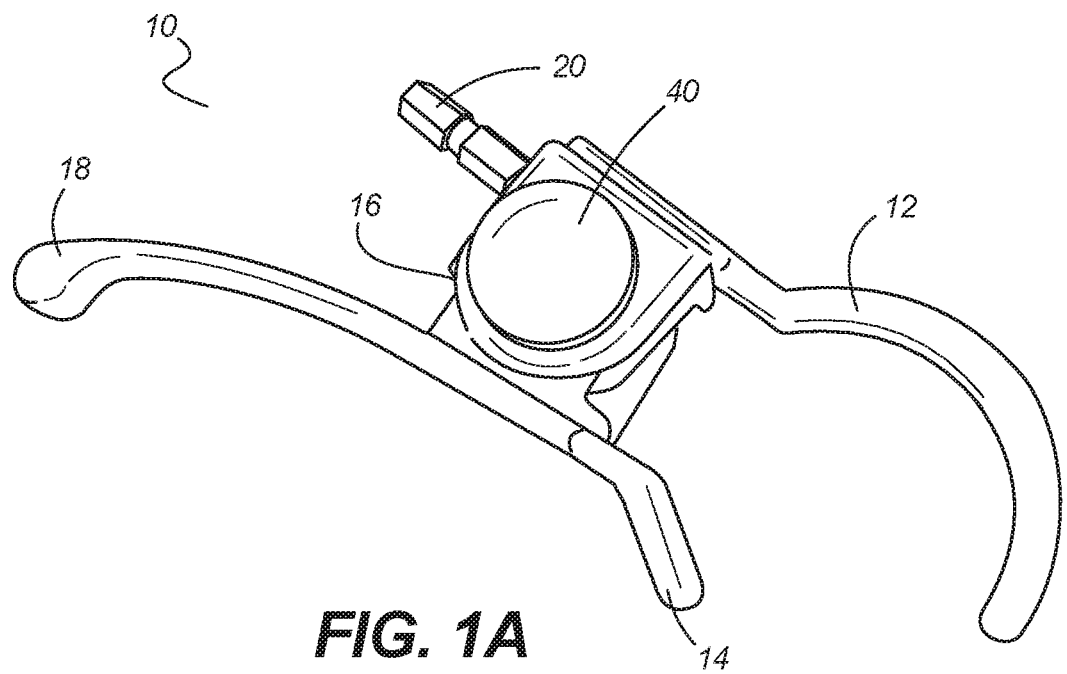
FIG. 1A is a perspective view of a releasable attachment device, according to one embodiment.
Figure 1B:
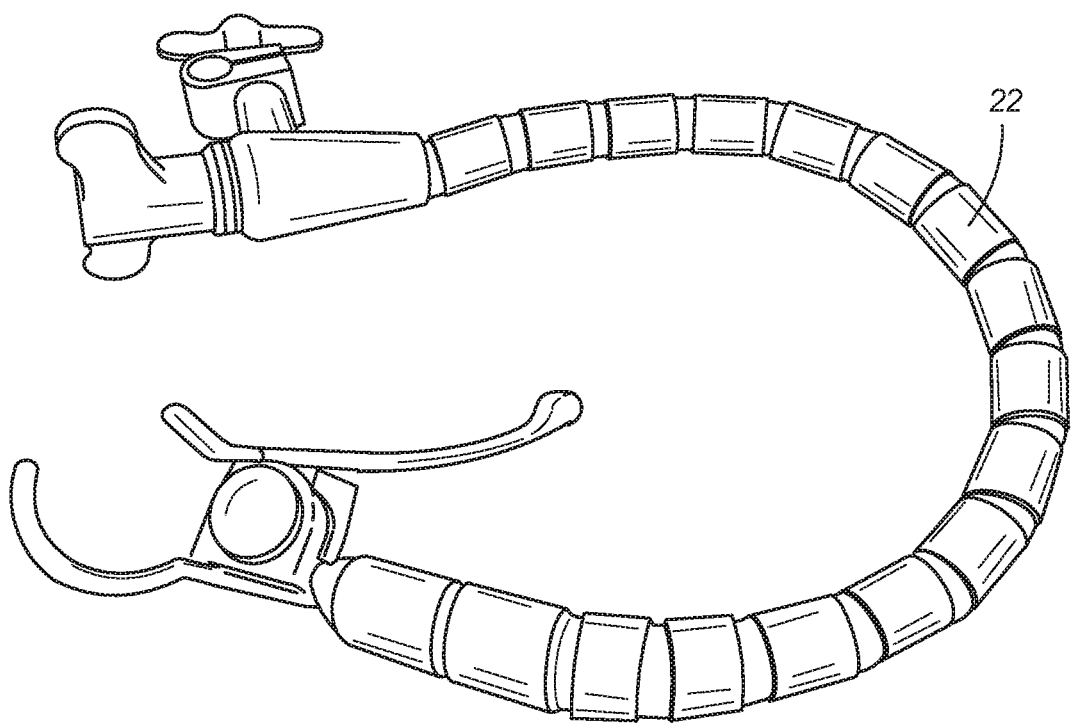
FIG. 1B is a perspective view of the releasable attachment device of FIG. 1A coupled to a flexible support arm, according to one embodiment.

In one embodiment as shown in FIGS. 1A, 1B, and 10, the attachment device (also referred to herein as a "clamp") 10 has a fixed or static jaw 12, a moveable or dynamic jaw 14, a hinge or joint 16, an actuation lever 18 coupled to the moveable jaw 14, a latch 40 operably coupled to the moveable jaw 14, and a coupling component or connection 20 for coupling the clamp 10 to a support arm such as a flexible support arm 22 as best shown in FIGS. 1B and 10. The moveable jaw 14 is moveably coupled to the fixed jaw 12 at the joint 16 and rotates in relation to the fixed jaw 12 via the joint 16.

The latch 40 (also referred to herein as an "actuation mechanism," "release mechanism," or "release button") is coupled to the moveable jaw 14 such that the latch 40 can be actuated to release the jaw 14 such that the jaw 14 is moveable in relation to the fixed jaw 12. This relationship between the latch 40 and the moveable jaw 14 will be described in greater detail below according to one embodiment. In certain implementations, the latch 40 can be actuated by depressing the latch 40 to "release" the moveable jaw 14 such that the user can actuate the actuation lever 18 to move the moveable jaw 14 to the desirable position. Alternatively, it is understood that any latch 40 configuration or mechanism can be used such that the latch 40 can be actuated to unlock and/or lock the moveable jaw 14.

In one embodiment, the actuation lever 18 is the proximal portion of a single rod or other structure in which the moveable jaw 14 constitutes the distal end thereof, as shown. Alternatively, the actuation lever 18 can be a separate component that is coupled to the moveable jaw 14 such that actuation of the lever 18 causes movement of the moveable jaw 14.

The flexible support arm 22, according to one implementation, is a known support arm: the Mediflex Flex Arm Plus™. In use, as best shown in FIG. 10, the flexible support arm 22 is coupled at its other end to a base support 24 that is, in turn, coupled to the surgical table 26 as shown. Alternatively, as best shown in FIG. 1D, the clamp 10 can be coupled at the coupling component 20 to a known non-flexible support arm 28. In one embodiment, the non-flexible support arm 28 is a Mediflex Strong Arm™. In a further alternative, the clamp 10 can couple to any known support arm or other type of support device for use with medical devices.

Figure 1C:
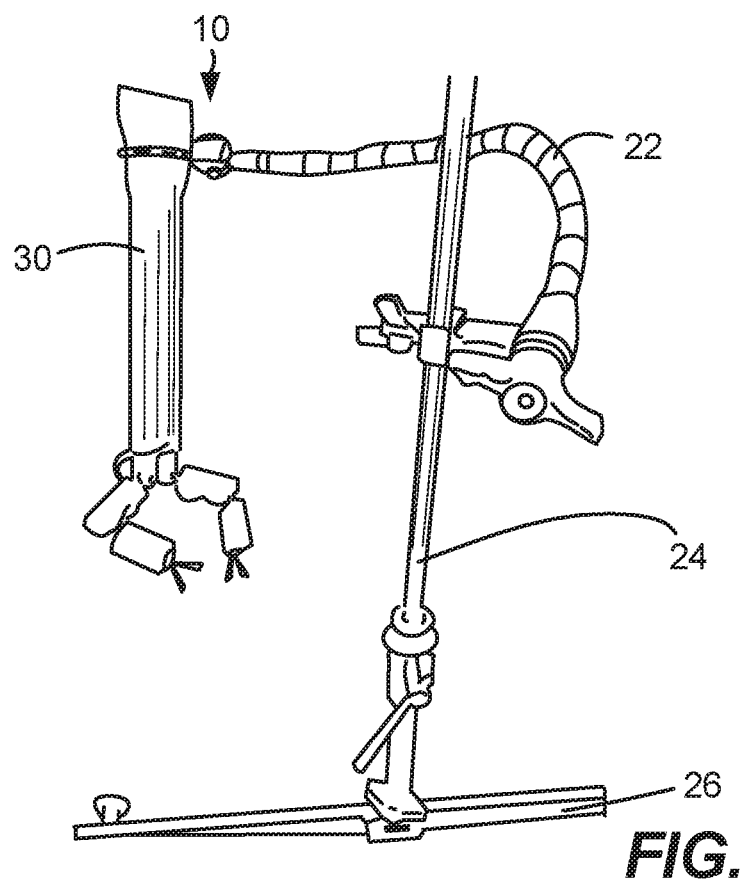
FIG. 1C is a perspective view of the releasable attachment device of FIG. 1A coupled to a flexible support arm and having a robotic device positioned within the jaws of the device, according to one embodiment.
Figure 1D:
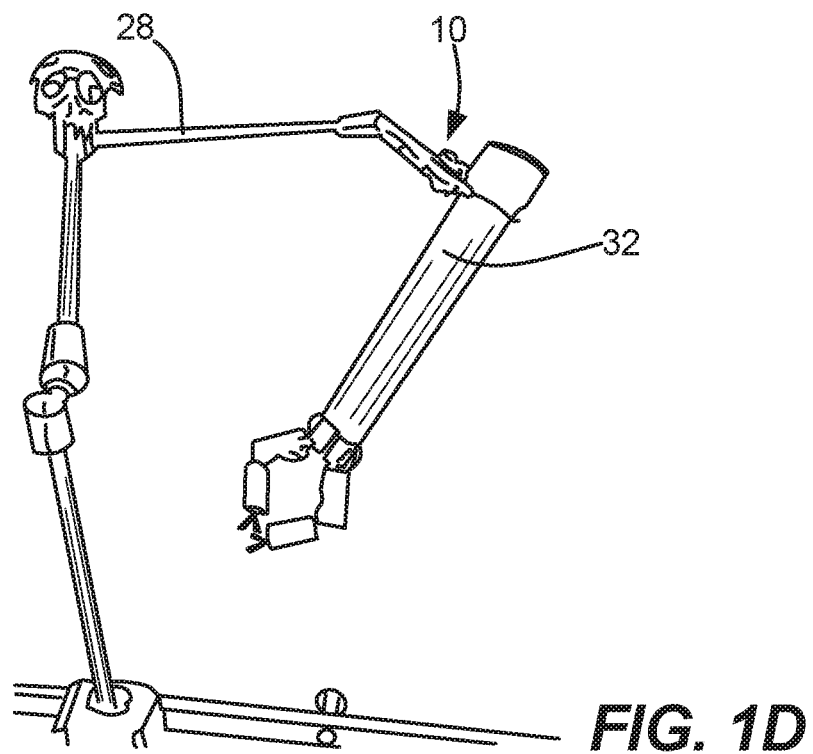
FIG. 1D is a perspective view of the releasable attachment device of FIG. 1A coupled to a rigid support arm and having a robotic device positioned within the jaws of the device, according to one embodiment.

As best shown in FIGS. 1C and 1D, the clamp 10 can be used to removably attach to a medical device. That is, the jaws 12, 14 define a space therebetween into which a target device can be positioned for coupling thereto. For example, in FIG. 10, the jaws 12, 14 of the clamp 10 are positioned around the robotic device 30 as shown such that a portion of the robotic device 30 is disposed within the space defined between the jaws 12, 14 such that the jaws 12, 14 retain the device 30 therebetween. According to another example as shown in FIG. 1D, the jaws 12, 14 of the clamp 10 are positioned around a different device 32. It is understood that the various clamp embodiments herein can be used to removably attach to any medical device, including any of the various medical devices and systems disclosed in U.S. Pat. No. 8,968,332 (issued on Mar. 3, 2015 and entitled "Magnetically Coupleable Robotic Devices and Related Methods"), U.S. Pat. No. 8,834,488 (issued on Sep. 16, 2014 and entitled "Magnetically Coupleable Surgical Robotic Devices and Related Methods"), U.S. patent application Ser. No. 14/617,232 (filed on Feb. 9, 2015 and entitled "Robotic Surgical Devices and Related Methods"), U.S. Pat. No. 9,579,088 (issued on Feb. 28, 2017 and entitled "Methods, Systems, and Devices for Surgical Visualization and Device Manipulation"), U.S. Pat. No. 8,343,171 (issued on Jan. 1, 2013 and entitled "Methods and Systems of Actuation in Robotic Devices"), U.S. Pat. No. 8,828,024 (issued on Sep. 9, 2014 and entitled "Methods and Systems of Actuation in Robotic Devices"), U.S. patent application Ser. No. 14/454,035 (filed Aug. 7, 2014 and entitled "Methods and Systems of Actuation in Robotic Devices"), U.S. patent application Ser. No. 12/192,663 (filed Aug. 15, 2008 and entitled Medical Inflation, Attachment, and Delivery Devices and Related Methods"), U.S. patent application Ser. No. 15/018,530 (filed Feb. 8, 2016 and entitled "Medical Inflation, Attachment, and Delivery Devices and Related Methods"), U.S. Pat. No. 8,974,440 (issued on Mar. 10, 2015 and entitled "Modular and Cooperative Medical Devices and Related Systems and Methods"), U.S. Pat. No. 8,679,096 (issued on Mar. 25, 2014 and entitled "Multifunctional Operational Component for Robotic Devices"), U.S. Pat. No. 9,179,981 (issued on Nov. 10, 2015 and entitled "Multifunctional Operational Component for Robotic Devices"), U.S. patent application Ser. No. 14/936,234 (filed on Nov. 9, 2015 and entitled "Multifunctional Operational Component for Robotic Devices"), U.S. Pat. No. 8,894,633 (issued on Nov. 25, 2014 and entitled "Modular and Cooperative Medical Devices and Related Systems and Methods"), U.S. Pat. No. 8,968,267 (issued on Mar. 3, 2015 and entitled "Methods and Systems for Handling or Delivering Materials for Natural Orifice Surgery"), U.S. Pat. No. 9,060,781 (issued on Jun. 23, 2015 and entitled "Methods, Systems, and Devices Relating to Surgical End Effectors"), U.S. patent application Ser. No. 14/745,487 (filed on Jun. 22, 2015 and entitled "Methods, Systems, and Devices Relating to Surgical End Effectors"), U.S. Pat. No. 9,089,353 (issued on Jul. 28, 2015 and entitled "Robotic Surgical Devices, Systems, and Related Methods"), U.S. patent application Ser. No. 14/800,423 (filed on Jul. 15, 2015 and entitled "Robotic Surgical Devices, Systems, and Related Methods"), U.S. patent application Ser. No. 13/573,849 (filed Oct. 9, 2012 and entitled "Robotic Surgical Devices, Systems, and Related Methods"), U.S. patent application Ser. No. 13/738,706 (filed Jan. 10, 2013 and entitled "Methods, Systems, and Devices for Surgical Access and Insertion"), U.S. patent application Ser. No. 13/833,605 (filed Mar. 15, 2013 and entitled "Robotic Surgical Devices, Systems, and Related Methods"), U.S. patent application Ser. No. 14/661,465 (filed Mar. 18, 2015 and entitled "Methods, Systems, and Devices for Surgical Access and Insertion"), U.S. Pat. No. 9,498,292 (issued on Nov. 22, 2016 and entitled "Single Site Robotic Devices and Related Systems and Methods"), U.S. patent application Ser. No. 15/357,663 (filed Nov. 21, 2016 and entitled "Single Site Robotic Devices and Related Systems and Methods"), U.S. Pat. No. 9,010,214 (issued on Apr. 21, 2015 and entitled "Local Control Robotic Surgical Devices and Related Methods"), U.S. patent application Ser. No. 14/656,109 (filed on Mar. 12, 2015 and entitled "Local Control Robotic Surgical Devices and Related Methods"), U.S. patent application Ser. No. 14/208,515 (filed Mar. 13, 2014 and entitled "Methods, Systems, and Devices Relating to Robotic Surgical Devices, End Effectors, and Controllers"), U.S. patent application Ser. No. 14/210,934 (filed Mar. 14, 2014 and entitled "Methods, Systems, and Devices Relating to Force Control Surgical Systems), U.S. patent application Ser. No. 14/212,686 (filed Mar. 14, 2014 and entitled "Robotic Surgical Devices, Systems, and Related Methods"), U.S. patent application Ser. No. 14/334,383 (filed Jul. 17, 2014 and entitled "Robotic Surgical Devices, Systems, and Related Methods"), U.S. patent application Ser. No. 14/853,477 (filed Sep. 14, 2015 and entitled "Quick-Release End Effectors and Related Systems and Methods"), U.S. patent application Ser. No. 14/938,667 (filed Nov. 11, 2015 and entitled "Robotic Device with Compact Joint Design and Related Systems and Methods"), U.S. patent application Ser. No. 15/227,813 (filed Aug. 3, 2016 and entitled "Robotic Surgical Devices, Systems, and Related Methods"), U.S. patent application Ser. No. 15/599,231 (filed May 18, 2017 and entitled "Robotic Surgical Devices, Systems, and Related Methods"), U.S. patent application Ser. No. 15/691,087 (filed Aug. 30, 2017 and entitled "Robotic Device with Compact Joint Design and an Additional Degree of Freedom and Related Systems and Methods"), U.S. Patent Application 62/425,149 (filed Nov. 22, 2016 and entitled "Improved Gross Positioning Device and Related Systems and Methods"), U.S. Patent Application 62/433,837 (filed Dec. 14, 2016 and entitled "Releasable Attachment Device for Coupling to Medical Devices and Related Systems and Methods"), and U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), and U.S. Pat. No. 8,179,073 (issued May 15, 2011, and entitled "Robotic Devices with Agent Delivery Components and Related Methods"), all of which are hereby incorporated herein by reference in their entireties.

Figure 2A:
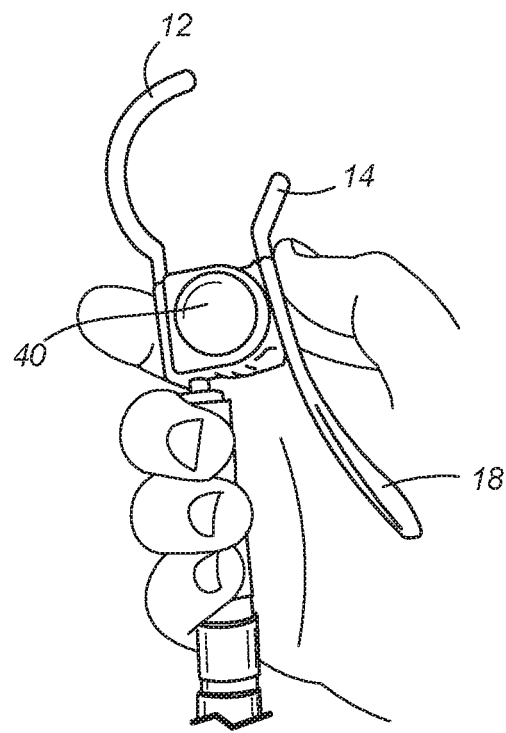
FIG. 2A is a side view of a releasable attachment device, according to one embodiment.
Figure 2B:
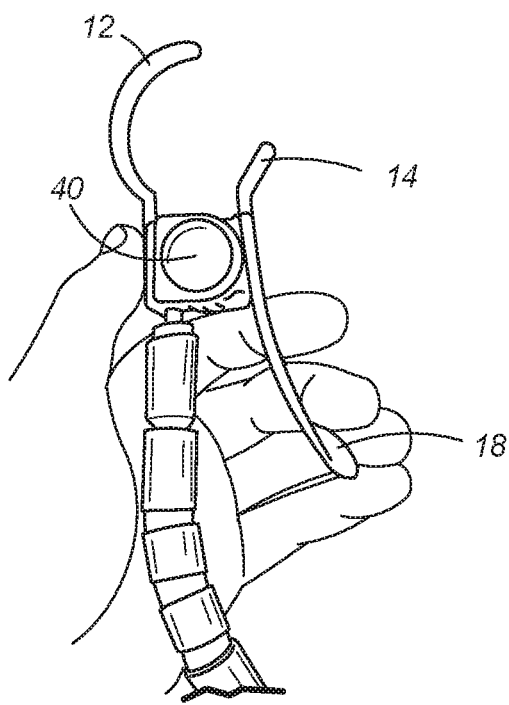
FIG. 2B is another side view of the releasable attachment device of FIG. 2A, according to one embodiment.
Figure 2C:
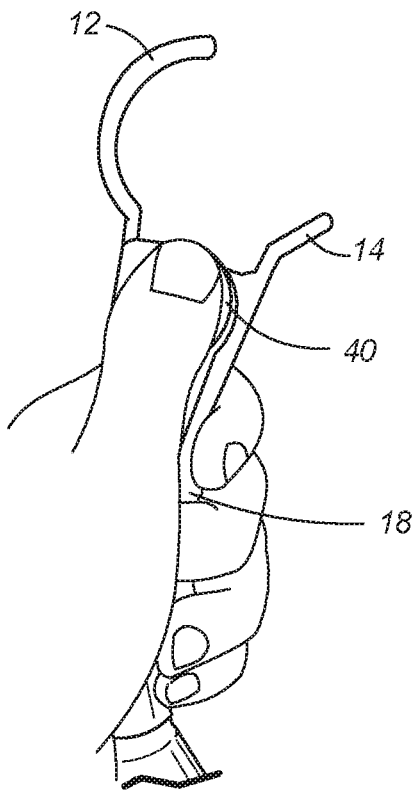
FIG. 2C is another side view of the releasable attachment device of FIG. 2A in which the jaws are in the open position, according to one embodiment.
Figure 4C:
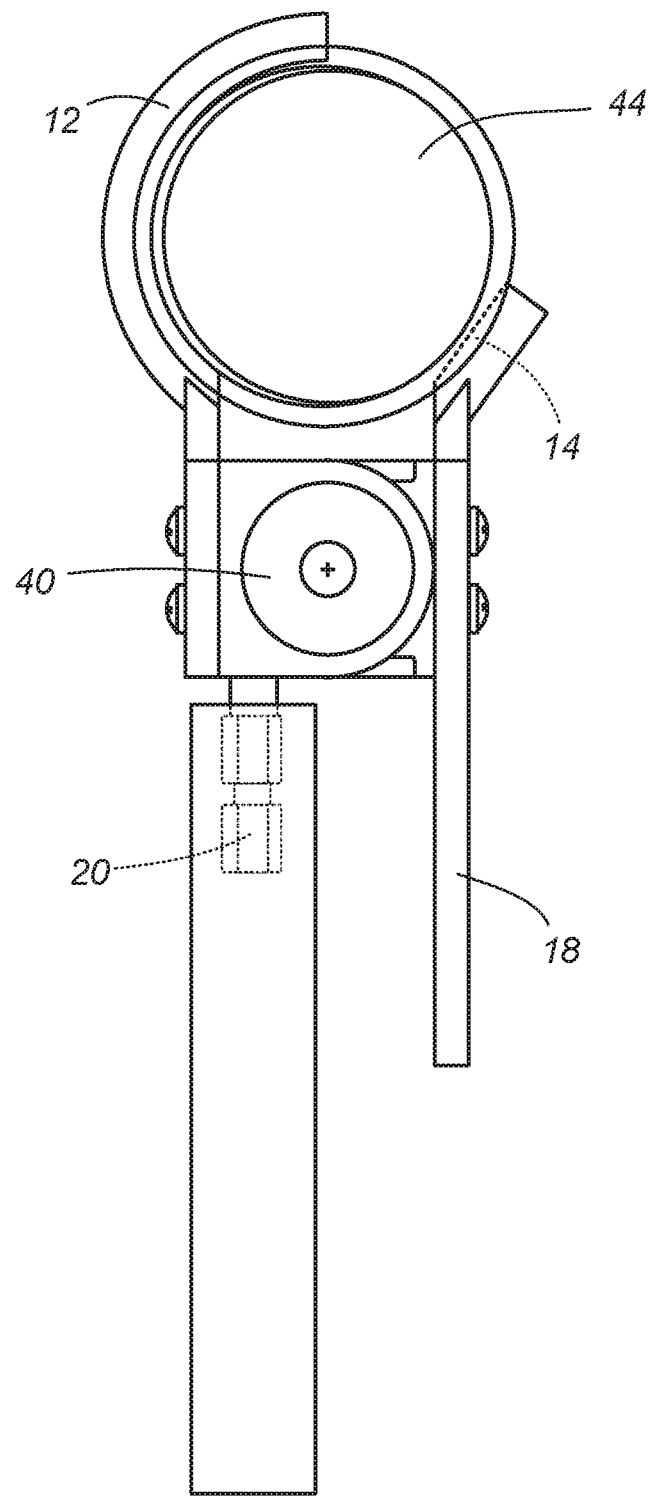
FIG. 4C is a side view of the releasable attachment device of FIG. 4A, according to one embodiment.

In use, as best shown in FIGS. 2A-2C, the device 10 can be used to removably attach to a robotic surgical device (such as devices 30, 32 or any other known device that can benefit from being coupled to a support arm, such as either of arms 22, 28 or any other known support device). In certain implementations, the jaws 12, 14 are configured to be positioned in grooves or channels defined in the robotic device. For example, FIGS. 4A and 4B depict a surgical device body 44 having a groove 46 defined therein as shown. The groove 46 is sized and configured to receive the jaws 12, 14 as shown.

Returning to FIGS. 2A-2C, the jaws 12, 14 of the device 10 have three main positions or configurations. The placement/removal (or "open") position is depicted in FIG. 2C, and it is the position in which the moveable jaw 14 is disposed at its widest configuration. That is, the moveable jaw 14 is disposed at the greatest possible distance from the fixed jaw 12 such that the space between them is the largest amount of any position. According to one embodiment, the moveable jaw 14 can be actuated to move into this open position by a user actuating both the depressable latch (or "button") and the actuation lever 18, as will be described in further detail below.

Another position is the fixed (also referred to as "closed" or "locked") position in which the jaws 12, 14 are at the closest possible proximity to each other. Once the device 10 is positioned with the jaws 12, 14 around the device body (such as body 44) while in the open configuration, the jaws 12, 14 can be moved into the closed position such that the jaws 12, 14 are disposed within the groove (such as groove 46) and securely disposed against the walls of the groove such that the body is held securely between the jaws 12, 14 and cannot move in relation to the jaws 12, 14. That is, the body cannot rotate or translate in relation to the jaws 12, 14. Alternatively, a device body without a groove can also be held by the jaws 12, 14 in the closed position.

The third position is the loosely closed (or "partially closed" or "relaxed") configuration in which the jaws 12, 14 are disposed close enough to each other in order to be disposed within the channel (such as channel 46) of the device body (such as body 44) for those devices having a groove, but with the jaws 12, 14 being sufficiently moveable in relation to each other such that the device body is rotatable in relation to the jaws 12, 14. That is, the jaws 12, 14 are disposed within the channel, but are not in sufficient contact with the walls of the channel to result in the necessary friction between the jaws 12, 14 and the walls to prevent the device body from rotatably moving in relation to the jaws 12, 14. This allows the device 10 to retain the surgical device in place while also allowing the surgical device to be rotated around the longitudinal axis of the device body. In certain implementations, this loosely closed configuration allows for the device body (such as body 44) to rotate up to, including, or more than 360°.

Figure 3A:
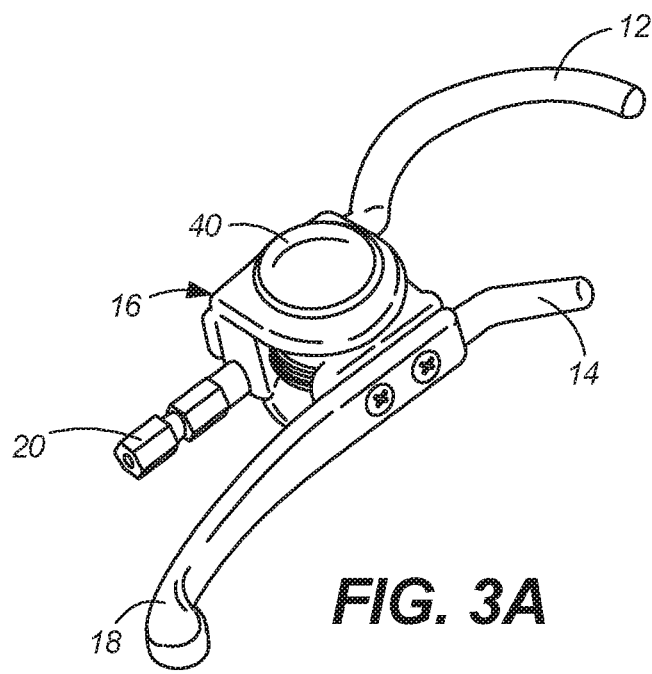
FIG. 3A is a perspective view of a releasable attachment device, according to one embodiment.

The various components that allow for the device 10 and the jaws 12, 14 to operate as described above will now be discussed in relation to FIGS. 3A-3C, according to one embodiment. The jaws 12, 14 are moveably coupled to each other via the first 16A and second 16B joint components that are coupled to and move in relation to each other. That is, the fixed jaw 12 is coupled to the first joint component (also referred to as a "first joint structure" and a "first joint bracket") 16A and the moveable jaw 14 is coupled to the second joint component (also referred to as a "second joint structure" and a "second joint bracket") 16B. The first bracket 16A has first and second struts that define two openings 52A, 52B, respectively that are aligned axially with each other such that the two openings 52A, 52B can form a single opening defined by the bracket 16A. Similarly, the second bracket 16B has first and second struts that define two openings 54A, 54B, respectively, that are aligned axially with each other such that the two openings 54A, 54B can form a single opening defined by the bracket 16B. The two joint components 16A, 16B are coupled to each other such that the openings 52A, 52B, 54A, 54B in each align along a single axis 50. A spring 42 is disposed within the two joint components 16A, 16B such that the spring 42 is operably coupled to both of the components 16A, 16B. That is, the first leg 42A of the spring 42 is coupled to the first joint component 16A and the second leg 42B is coupled to the second component 16B such that the spring 42 urges the two joint components 16A, 16B such that the jaws 12, 14 are urged toward the closed position. Thus, with no other forces applied to the device 10, the jaws 12, 14 are continuously urged toward the closed configuration by the spring 42.

Figure 3B:
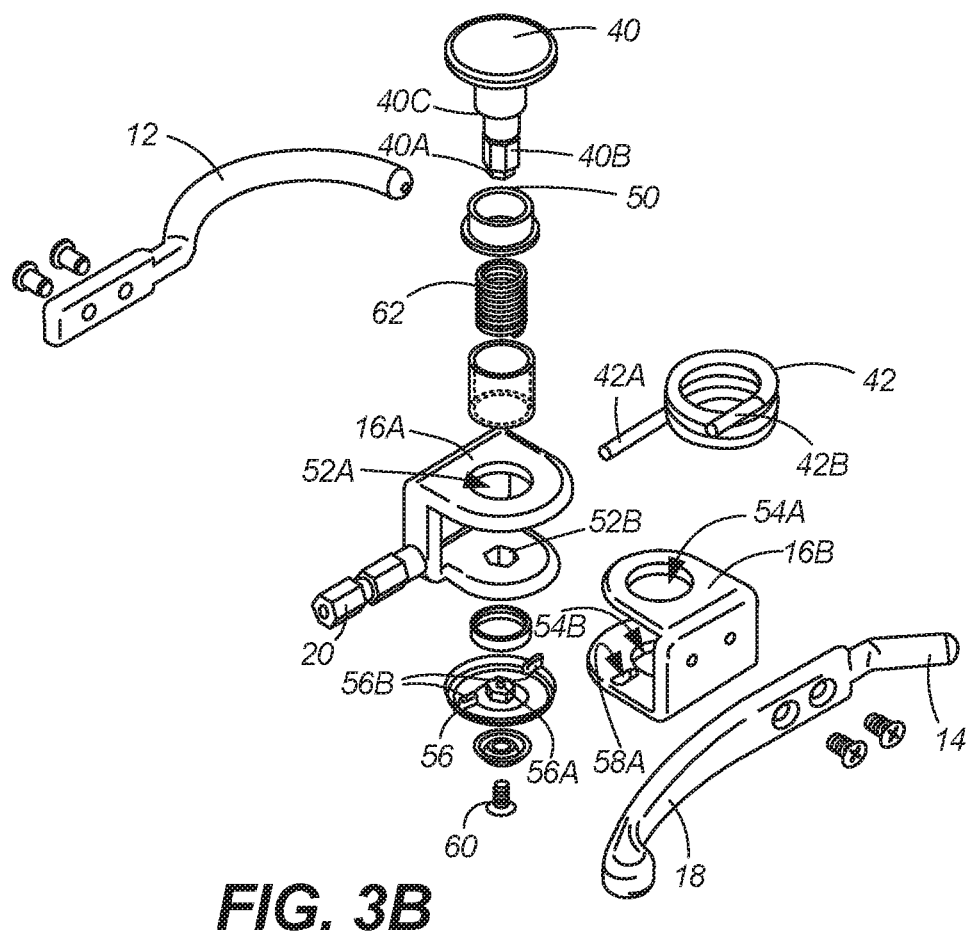
FIG. 3B is an exploded schematic view of the various components of the releasable attachment device of FIG. 3A, according to one embodiment.

In certain implementations, disposed through the openings 52A, 52B, 54A, 54B of the joint components 16A, 16B is the latch 40 and related components. The latch 40 has two hex configurations 40A, 40B defined along a distal portion of its length, as best shown in FIGS. 3B and 3C. Alternatively, any shapes that allow for rotational coupling can be envisioned. The latch 40 also has a shoulder 40C defined or otherwise disposed along its length. The first hex configuration 40A can be disposed through and coupled to the hex-shaped opening 56A in the lock ring 56 such that the lock ring 56 and the latch 40 are rotationally constrained in relation to each other permanently. That is, regardless of the axial position of the latch 40, the lock ring 56 remains coupled to and rotationally constrained to the latch 40. Further, the lock ring 56 has projections 56B that can be disposed within the openings 58A, 58B defined in the second joint component 16B such that the lock ring 56 and second joint component 16B are rotationally constrained in relation to each other when the latch 40 is in its non-depressed position. However, the openings 58A, 58B are slightly larger than the projections 56B such that the projections 56B can move within the openings 58A, 58B. For example, the projections 56B can, according to certain embodiments, move within the openings 58A, 58B in relation to the second joint component 16B sufficiently to allow the jaws 12, 14 to move in relation to each other enough to allow the device body (such as body 44) to rotate in relation to the jaws 12, 14 but not so much that the jaws 12, 14 are no longer disposed in the channel (such as channel 46) in the device body. The second hex configuration 40B can be disposed through and coupled to the hex-shaped opening 52B in the first joint component 16A such that the joint component 16A and the latch 40 are rotationally constrained in relation to each other permanently. That is, the latch 40 remains rotationally constrained to the joint component 16A whether the latch 40 is in its depressed position or its non-depressed position. The latch 40 is retained in its coupling to the two joint components 16A, 16B via the attachment screw 60 that is coupled to the distal end of the latch 40. Alternatively, the latch 40 can be similarly coupled to the various components discussed above utilizing any known configurations or mechanisms.

In this specific embodiment, the latch 40 can be moved in a translational fashion (axially) by depressing the top portion (the button portion) of the latch 40. The latch 40 is continuously urged upward away from the two joint components 16A, 16B by the spring 62 that is disposed around the latch 40 and between the bottom portion of the first joint component 16A and the shoulder 40C of the latch 40. That is, the spring 62 is tensioned such that it is constantly urging the shoulder 40C and thus the latch 40 away from the bottom portion of the first joint component 16A. As such, with no outside force (such as a user's finger or thumb depressing the latch 40 downward), the default state of the latch 40 is the upward or undepressed position in which the two protrusions 56B are disposed within the openings 58A, 58B of the bottom portion of the second joint component 16B, thereby resulting in the second joint component 16B being rotationally constrained to the lock ring 56. Thus, when the latch 40 is in its undepressed position such that the second joint component 16B is rotationally constrained to the lock ring 56, the moveable jaw 14 that is coupled to the second joint component 16B is rotationally constrained as well. As a result, the default state of the device 10 is for the second joint component 16B to be rotationally constrained to the lock ring 56 and therefore only able to move in relation to the first joint component 16A by the amount of space between the protrusions 56B and the openings 58A, 58B as described above, thus resulting in the device 10 being in the relaxed configuration as described above. This relaxed configuration can be utilized by a user depressing the actuation lever 18, thereby urging the jaw 14 away from the jaw 12 by the amount of distance allowed by the additional space between the projections 56B and the openings 58A, 58B, which can eliminate the frictional force between the jaws 12, 14 and the device body, thereby allowing rotation of the body in relation to the jaws 12, 14. On the other hand, if the user is not depressing the actuation lever 18, the spring 42 is urging the jaws 12, 14 together, creating frictional force between the jaws 12, 14 and the device body, thereby resulting in the locked configuration.

To actuate the device 10 to move into the open configuration, according to one embodiment, the user can depress the latch 40, which urges the latch 40 distally, which causes the lock ring 56 to move distally, thereby urging the projections 56B out of the openings 58A, 58B, which "uncouples" the second joint component 16B from the lock ring 56. Once the projections 56B are no longer disposed within the openings 58A, 58B, the lock ring 56 is no longer rotationally constrained to the second joint component 16B, thereby allowing the second joint component 16B to rotate in relation to the first joint component 16A such that the jaw 14 can be moved into the open configuration as discussed above.

It is understood that the two jaws 12, 14 depicted can be replaced with jaws of any shape or configuration. As such, the jaws 12, 14 can couple to device bodies of any known shape or configuration.

Although the present invention has been described with reference to preferred embodiments, persons skilled in the art will recognize that changes may be made in form and detail without departing from the spirit and scope of the invention.

What is claimed is:

1. A releasable attachment device for use with surgical tools, the device comprising: (a) a fixed jaw fixedly coupled to a joint housing; (b) a moveable jaw rotationally coupled to the joint housing, the moveable jaw comprising an open position and a closed position; (c) an actuation mechanism operably coupled to the joint housing, wherein the actuation mechanism comprises a locked position and a released position; and (d) an actuation structure operably coupled to the moveable jaw, wherein the joint housing comprises: (a) a stationary joint structure comprising a first opening defined therethrough;
(b) a pivotable joint structure comprising a second opening defined therethrough and at least one rotational coupling mechanism defined therein; (c) the actuation mechanism disposed through the first and second openings, wherein the actuation mechanism is rotationally coupled to the first joint structure; and (d) a locking structure rotationally coupled to a distal end of the actuation mechanism and detachably coupleable with the at least one rotational coupling mechanism.

2. The releasable attachment device of claim 1, further comprising a coupling component fixedly coupled to the joint housing, wherein the coupling component comprises a coupling structure constructed and arranged to couple to an external support device.

3. The releasable attachment device of claim 1, further comprising a tension component operably coupled to the joint housing, wherein the tension component is constructed and arranged to urge the moveable jaw toward the closed position.

4. The releasable attachment device of claim 1, further comprising a tension component operably coupled to the actuation mechanism, wherein the tension component is constructed and arranged to urge the actuation mechanism toward the locked position.

5. The releasable attachment device of claim 1, wherein the fixed jaw and moveable jaw are constructed and arranged to couple with a surgical tool in a groove defined around an outer surface of the surgical tool.

6. The releasable attachment device of claim 1, wherein the released position comprises the actuation mechanism positioned distally in relation to the locked position.

7. The releasable attachment device of claim 1, wherein the locking structure is coupled to the at least one rotational coupling mechanism when the actuation mechanism is in the locked position and wherein the locking structure is not coupled to the at least one rotational coupling mechanism when the actuation mechanism is in the released position.

8. The releaseable attachment device of claim 1, wherein the pivotable joint structure is rotatable in relation to the stationary joint structure when the actuation mechanism is in the released position.

9. A releasable attachment device for use with surgical tools, the device comprising:
   (a) a joint housing comprising:
      (i) a first joint structure comprising a first opening defined therethrough; and
      (ii) a second joint structure comprising a second opening defined therethrough and at least one rotational coupling mechanism defined therein;
      (iii) an actuation mechanism disposed through the first and second openings, wherein the actuation mechanism is rotationally coupled to the first joint structure and wherein the actuation mechanism comprises an undepressed axial position and a depressed axial position; and
      (iv) a locking structure rotationally coupled to a distal end of the actuation mechanism and detachably coupleable with the at least one rotational coupling mechanism;

(b) a fixed jaw fixedly coupled to the first joint structure;

(c) a moveable jaw fixedly coupled to the second joint structure, the moveable jaw comprising an open position and a closed position; and (d) an actuation structure operably coupled to the moveable jaw.

10. The releasable attachment device of claim 9, further comprising a coupling component fixedly coupled to the joint housing, wherein the coupling component comprises a coupling structure constructed and arranged to couple to an external support device.

11. The releasable attachment device of claim 9, further comprising a tension component operably coupled to the first joint structure and the second joint structure, wherein the tension component is constructed and arranged to urge the moveable jaw toward the closed position.

12. The releasable attachment device of claim 9, further comprising a tension component operably coupled to the actuation mechanism, wherein the tension component is constructed and arranged to urge the actuation mechanism toward the undepressed axial position.

13. The releasable attachment device of claim 9, wherein the fixed jaw and moveable jaw are constructed and arranged to couple with a surgical tool in a groove defined around an outer surface of the surgical tool.

14. The releasable attachment device of claim 9, wherein the depressed axial position comprises the actuation mechanism positioned distally in relation to the undepressed axial position.

15. The releasable attachment device of claim 9, wherein the locking structure is coupled to the at least one rotational coupling mechanism when the actuation mechanism is in the undepressed axial position and wherein the locking structure is not coupled to the at least one rotational coupling mechanism when the actuation mechanism is in the depressed axial position.

16. The releasable attachment device of claim 9, wherein the second joint structure is rotatable in relation to the first joint structure when the actuation mechanism is in the depressed axial position.

17. A releasable attachment device for use with surgical tools, the device comprising:

(a) a housing comprising:
  (i) a first joint structure comprising:
    (A) a first strut comprising a first opening; and
    (B) a second strut comprising a second opening, wherein the second opening comprises a first rotational coupling mechanism;
  (ii) a second joint structure comprising
    (A) a third strut comprising a third opening; and
    (B) a fourth strut comprising a fourth opening and a second rotational coupling mechanism;
  (iii) an actuation mechanism comprising a mechanism body and a button coupled thereto, wherein the mechanism body is disposed through the first, second, third, and fourth openings, wherein the mechanism body is coupled to the rotational coupling mechanism such that the mechanism body is rotationally constrained to the second strut, and wherein the actuation mechanism comprises an undepressed axial position and a depressed axial position; and
  (iv) a locking structure rotationally coupled to a distal end of the mechanism body and detachably coupleable with the second rotational coupling mechanism, wherein the locking structure is coupled to the second rotational coupling mechanism when the actuation mechanism is in the undepressed axial position and wherein the locking structure is not coupled to the second rotational coupling mechanism when the actuation mechanism is in the depressed axial position,
  wherein the second joint structure is rotatable in relation to the first joint structure when the actuation mechanism is in the depressed axial position;

(b) a fixed jaw fixedly coupled to the first joint structure;

(c) a moveable jaw fixedly coupled to the second joint structure, the moveable jaw comprising an open position and a closed position; and (d) an actuation structure operably coupled to the moveable jaw.

18. The releasable attachment device of claim 17, further comprising a coupling component fixedly coupled to the housing, wherein the coupling component comprises a coupling structure constructed and arranged to couple to an external support device.

19. The releasable attachment device of claim 17, further comprising a tension component operably coupled to the first and second joint structures, wherein the tension component is constructed and arranged to urge the moveable jaw toward the closed position.

* * * * *